United States Patent [19]
Zinnen et al.

[11] Patent Number: 5,770,783
[45] Date of Patent: Jun. 23, 1998

[54] ALKANE ISOMERIZATION USING REVERSIBLE FLOW REACTIVE CHROMATOGRAPHY

[75] Inventors: Herman A. Zinnen, Evanston; Charles P. McGonegal, Addison, both of Ill.

[73] Assignee: UOP LLC, Des Plaines, Ill.

[21] Appl. No.: 794,250

[22] Filed: Feb. 3, 1997

[51] Int. Cl.$^6$ .................................................. C07C 5/13
[52] U.S. Cl. ........................ 585/738; 585/702; 585/735; 585/738; 585/737; 585/739; 585/744; 585/748; 585/750; 585/751
[58] Field of Search ..................................... 585/702, 735, 585/738, 739, 744, 737, 748, 750, 751

[56] References Cited

U.S. PATENT DOCUMENTS

| | | | |
|---|---|---|---|
| 3,122,494 | 2/1964 | Brown et al. | 208/63 |
| 4,783,574 | 11/1988 | Barnes | 585/738 |
| 4,804,802 | 2/1989 | Evans et al. | 585/734 |
| 4,855,529 | 8/1989 | Stem et al. | 585/737 |
| 5,059,741 | 10/1991 | Foley | 585/734 |
| 5,146,037 | 9/1992 | Zarchy et al. | 585/738 |
| 5,245,102 | 9/1993 | Zarchy et al. | 585/738 |
| 5,345,026 | 9/1994 | Chang et al. | 585/700 |
| 5,530,172 | 6/1996 | Funk et al. | 585/736 |
| 5,530,173 | 6/1996 | Funk et al. | 585/737 |

OTHER PUBLICATIONS

Badger, C.M.A., Harris, J.A.; Scott, K.F.; Walker, M.J.; Phillips, C.S.G.; *J. Chromatogr.*, 1976, 126, 11–18.

*Primary Examiner*—Glenn Caldarola
*Assistant Examiner*—Thuan D. Dang
*Attorney, Agent, or Firm*—Thomas K. McBride; Eugene I. Snyder; Maryann Maas

[57] ABSTRACT

A process to isomerize at least one normal or mono-methyl-branched alkane containing from about 6 to about 8 carbon atoms to form at least one multi-methyl-branched alkane has been developed. The normal or mono-methyl-branched alkane is introduced to a reaction and adsorption zone operating under conditions effective to isomerize the normal or mono-methyl-branched alkane and containing a catalyst effective to isomerize the normal or mono-methyl-branched alkane and an adsorbent effective to selectively adsorb normal and mono-methyl-branched alkanes relative to multi-methyl-branched alkanes. Hydrogen and a desorbent comprising at least one alkane having from about 4 to about 8 carbon atoms is introduced to a first portion of the reaction and adsorption zone and an effluent containing at least one multi-methyl-branched alkane is withdrawn from a second portion of the reaction and adsorption zone. After a period of time, the desorbent is redirected to the second portion of the reaction and adsorption zone and concurrently the effluent containing at least one multi-methyl-branched alkane is withdrawn from the first portion of the reaction and adsorption zone. The alternation of introducing the desorbent to a first portion and then a second portion of the reaction and adsorption zone while concurrently withdrawing the effluent from the second portion and then the first portion of the reaction and adsorption zone is continued.

20 Claims, 2 Drawing Sheets

ALKANE ISOMERIZATION USING REVERSIBLE FLOW REACTIVE CHROMATOGRAPHY

BACKGROUND OF THE INVENTION

Alkane isomerization processes are widely used by refiners to convert normal and mono-methyl-branched $C_6$ alkanes into more valuable branched alkanes. The multi-methyl-branched $C_6$ alkanes have a higher octane number and are used as gasoline blending components to boost the octane number of the gasoline. Normal and mono-methyl-branched $C_7$ alkanes have been converted into benzene and other valuable aromatic hydrocarbons for gasoline blending by catalytic reforming. However, due to environmental concerns, the demand for aromatics in the future may diminish. An alternate refining process for the normal and mono-methyl-branched $C_7$ and $C_8$ alkanes that yields a high octane number product is the present invention of alkane isomerization by reversible flow reactive chromatography. The isomerized $C_7$ and $C_8$ products may be used as octane number boosters in gasoline blending instead of benzene and other aromatics.

Typically, commercial isomerization processes have had at least a two-stage design; the first stage is a fixed bed reactor and the second stage is a separation unit, see for example U.S. Pat. Nos. 5,146,037 and 5,245,102. The isomerization that takes place in the fixed bed reactor is limited by thermodynamic equilibrium which results in the reactor effluent containing a substantial amount of unconverted alkanes. The separation unit, which is usually either an adsorption or a fractionation unit, is used to separate the unconverted alkanes from the isomerized product alkanes. The adsorption unit may be one or more beds of different adsorbent each performing a different separation as in U.S. Pat. Nos. 5,059,741, 4,855,529 and 4,804,802. The unconverted alkanes are generally recycled to the fixed bed reactor. With this type of design, the recycle stream is usually substantial, and methods of increasing the yield of highly branched alkanes are in demand.

The present invention makes use of reversible flow reactive chromatography to perform isomerization of hydrocarbons containing from about 6 to about 8 carbon atoms. Reactive chromatography in general allows for concurrent isomerization and separation of the unconsumed reactants from the products, thereby extending product yields beyond thermodynamic equilibrium limitations. Isomerization by simulated moving bed reactive chromatography has been described in U.S. Pat. Nos. 5,530,172 and 5,530,173. Isomerization by fixed bed reactive chromatography was disclosed in Badger, C. M. A.; Harris, J. A.; Scott, K. F.; Walker, M. J.; Phillips, C. S. G. *J. Chromatogr.* 1976, 126, 11–18, where a catalyst was placed in a gas chromatography column and a heater was moved along the length of the column to catalyze isomerization and effect separation.

U.S. Pat. No. 4,783,574 described reversing a sweep fluid flow over separate zones of catalyst and adsorbent. A fixed bed reactor contained a sub-bed of adsorbent at each end and one sub-bed of catalyst in the center. The feed was introduced near the catalyst sub-bed, and a sweep fluid was introduced at one end of the reactor. The isomerization was catalyzed and unconsumed reactants were adsorbed on the adsorbent sub-bed downstream of the catalyst sub-bed in the direction of the desorbent flow. Then the sweep fluid flow was reversed by introducing the desorbent from the opposite end of the reactor to sweep the unconsumed reactants and carry them back to the catalyst sub-bed.

U.S. Pat. No. 3,122,494 described two sub-beds containing a mixture of catalyst and adsorbent where the feed is introduced between the two sub-beds and the desorbent introduction is alternated between the first sub-bed and the second sub-bed. The adsorbent must selectively adsorb straight-chain hydrocarbons to the substantial exclusion of non-straight-chain hydrocarbons, and the desorbent is hydrogen which is completely inert in the isomerization reaction.

The above reversible flow operations are designed to reduce normal alkane content without specificity as to desired branched products. The reversible flow fixed bed references do not teach separating multi-methyl-branched alkanes from normal and mono-methyl-branched alkanes in order to optimize the process for specifically multi-methyl branched alkane production. The reversible flow fixed bed references also fail to teach desorbents that are effective for chromatographic separation. The present invention uses reversible flow reactive chromatography to isomerize alkanes having from about 6 to about 8 carbon atoms and to concurrently separate product multi-methyl-branched alkanes from normal and mono-methyl-branched alkanes. Furthermore, in the present invention the desorbent is an alkane, thus eliminating a need for regeneration of the adsorbent as required in the previous references which use hydrogen to purge unreacted alkanes from the adsorbent.

SUMMARY OF THE INVENTION

The purpose of the invention is to isomerize at least one normal or mono-methyl-branched alkane containing from about 6 to about 8 carbon atoms to form at least one multi-methyl-branched alkane. The normal or mono-methyl-branched alkane is introduced to a fixed bed reaction and adsorption zone operating under conditions effective to isomerize the normal or mono-methyl-branched alkane and containing a catalyst effective to isomerize the alkane and an adsorbent effective to selectively adsorb normal and mono-methyl-branched alkanes relative to multi-methyl-branched alkanes. Hydrogen and a desorbent comprising at least one alkane having from about 4 to about 8 carbon atoms is introduced to a first portion of the reaction and adsorption zone and an effluent containing at least one multi-methyl-branched alkane is withdrawn from a second portion of the reaction and adsorption zone. After a period of time, the desorbent is redirected to the second portion of the reaction and adsorption zone and concurrently the effluent containing at least one multi-methyl-branched alkane is withdrawn from the first portion of the reaction and adsorption zone. The alternation of introducing the desorbent to a first portion and then a second portion of the reaction and adsorption zone while concurrently withdrawing the effluent from the second portion and then the first portion of the reaction and adsorption zone is continued.

It is preferred that the catalyst and adsorbent be present as a mixture and most preferred that the mixture be homogeneous. A specific embodiment of the invention is one where the feed is introduced to the same portion of the reaction and adsorption zone as the desorbent is introduced, with the feed being introduced in a pulsed manner. Periodically the location of the feed and desorbent input is alternated between a first portion of the zone and a second portion of the zone. Another specific embodiment of the invention is one where the feed and desorbent are both continuously introduced to the reaction and adsorption zone. The feed is introduced at a location so that the zone is symmetrically disposed about the feed with respect to size, flow capacity, and adsorbent and catalyst distribution thereby dividing the zone into two equivalent portions. The position of the feed input remains constant while periodically the desorbent input is alternated between the first portion of the zone and the second portion of the zone.

DETAILED DESCRIPTION OF THE INVENTION

Figure 1:
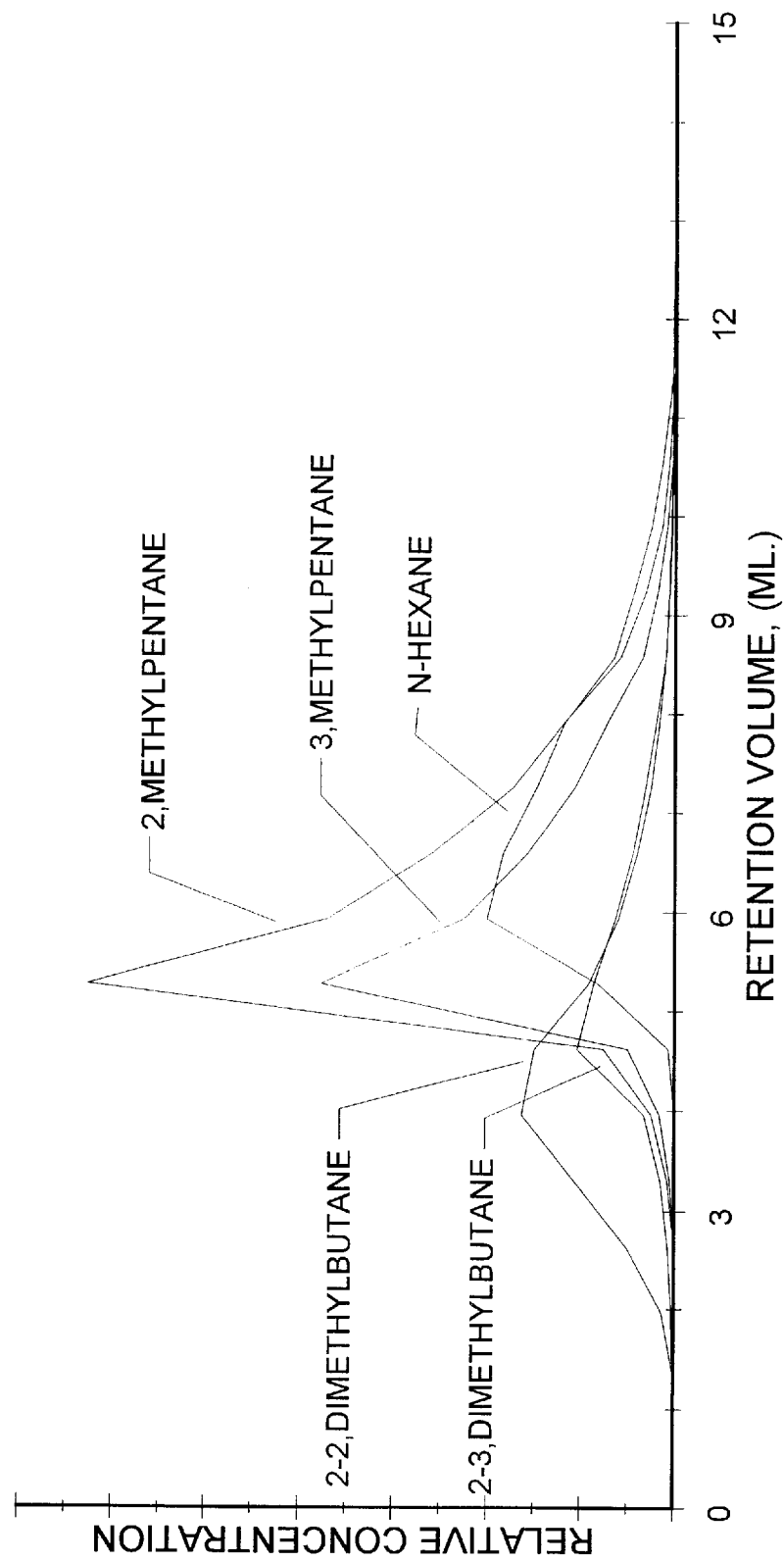
FIG. 1 is a chromatogram showing the results of the isomerization of a pulse of normal hexane and the separation of a high multi-methyl-branched fraction from a mixture of normal, mono-methyl-branched and multi-methyl-branched alkanes using a mixture of platinum on tungstated zirconia and silicalite as conducted in Example 1.

This invention is a process for surpassing the equilibrium limitations of an alkane isomerization reaction to produce valuable multi-methyl-branched alkanes using reversible flow reactive chromatography. In general terms, the invention is carried out by introducing a reactant alkane to a zone containing both a catalyst effective for isomerization and an adsorbent capable of adsorbing normal and mono-methyl-branched alkanes relative to multi-methyl-branched alkanes. Hydrogen and a desorbent containing an alkane having from 4 to about 8 carbon atoms are also introduced to the zone containing the catalyst and adsorbent. The reactant alkane is isomerized with the aid of the catalyst and the isomerized products may consist of mono-methyl-branched alkanes and multi-methyl-branched alkanes. The desired multi-methyl-branched alkanes are immediately separated from any unreacted normal alkane reactant or mono-methyl-branched alkane which are adsorbed by the adsorbent. The multi-methyl-branched alkane product will be least adsorbed by the adsorbed by the adsorbent relative to the normal and mono-methyl-branched alkanes and so will be carried unhindered with the flow of the desorbent and removed from the zone. Due to the dynamic equilibrium of the adsorbent with components constantly being adsorbed and desorbed, a band of normal and mono-methyl-branched alkanes will gradually move through the zone and will eventually reach the point where the multi-methyl-branched alkanes are being withdrawn from the zone. To avoid contaminating the product effluent with the band of normal and mono-methyl-branched alkanes, the introduction of the desorbent is changed to a different location in the zone so that the flow of desorbent is now reversed through the zone. The location where the product effluent is withdrawn is also moved to remain downstream of the desorbent. Due to the continuous separation and removal of the multi-methyl-branched alkane, the thermodynamic equilibrium constraint of a static system is no longer a limiting factor, and the isomerization continues thereby resulting in a much greater conversion to valuable isomerized alkanes.

As discussed above, it is a requirement that the reaction and adsorption zone contain a catalyst effective for isomerization. Such catalysts are well known in the art and suitable catalysts include, but are not limited to, platinum on mordenite, aluminum chloride on alumina, and platinum on sulfated or tungstated metal oxides such as zirconia. See generally, Kirk-Othmer *Encyclopedia of Chemical Technology,* 3rd ed.; Grayson, M., Eckroth, D., Eds.; John Wiley & Sons: New York, Vol. 11 p 664, Vol. 12 pp 911 and 922, and Vol. 15 p 651. Depending upon the composition of the feed, several different catalysts may be combined in order to accomplish the catalysis function. When choosing a catalyst, the operating temperature of the adsorbent that will be used must be considered. Both the adsorbent and the catalyst must be able to perform their respective functions at the same operating temperature. The reaction and adsorption zone may be operated at typical hydrocarbon isomerization operating conditions including temperatures ranging from 100° to 300° C. and pressures from atmospheric to 500 psig. The operating conditions should be chosen so that all components are in the same phase, gas or liquid. Since many of the suitable adsorbents perform better at lower temperatures, the preferred catalysts are platinum on tungstated zirconia or platinum on sulfated zirconia due to their high activity at lower temperatures. These catalysts are further preferred since operating at lower temperatures reduces the likelihood that the higher carbon atom compounds will undergo cracking.

It is also required that the reaction and adsorption zone contain an adsorbent. The adsorbent is selected to have either a pore size capable of admitting normal or mono-methyl-branched alkane reactants but not the multi-methyl-branched isomerized products or to have an affinity for alkanes with no or low branching. In other words, the adsorbent must adsorb mono-methyl-branched alkanes relative to multi-methyl-branched alkanes. Any adsorbent meeting this criteria may be used in the process. Examples of suitable adsorbents include, but are not limited to, ferrierite, silicalite and zeolites having the structural framework of X, Y, or beta, and ion exchanged with sodium, potassium, calcium, strontium, barium, or mixtures thereof. The zeolites may be ion exchanged with transition metal ions, but this is less preferred due to the tendency for increased cracking with these ions. When the feed alkanes are a mixture of $C_6$ and $C_7$ alkanes, the most preferred adsorbent is silicalite. However, when the feed alkanes are either only $C_6$ alkanes or only $C_7$ alkanes, the most preferred adsorbent is a sodium exchanged X-type zeolite.

The catalyst and adsorbent may be present in the fixed bed reaction and adsorption zone in a variety of ways, with the catalyst to adsorbent ratio ranging from about 0.01 to about 1.0. It is preferred that the particles be present in a mixture and it is most preferred that the mixture be a homogeneous mixture of adsorbent and catalyst particles which is distributed throughout the zone. Although less preferred, it is possible that the particles may be structured in alternating layers, sections, or cells as is known in the reactive chromatography art. For example, a vessel could contain a thin layer of catalyst followed by a thin layer of adsorbent with the pattern repeating throughout the vessel. The zone itself may be all contained within a single vessel, or may be composed of a series of two or more sub-beds that are sequentially connected. It is important, however, that the catalyst and adsorbent be structured so that the zone is capable of performing reactive chromatography where the products are rapidly separated from reactants. Therefore, it would be unacceptable to have, for example, the zone consist of only two sub-beds, one containing only catalyst and the other containing only adsorbent, or only three sub-beds with a catalyst-only sub-bed between two adsorbent-only sub-beds. To perform reactive chromatography the catalyst and adsorbent must be of sufficient integration with one another so that the equilibrium limitations of a fixed bed system are overcome. Furthermore, if the catalyst and adsorbent were not sufficiently integrated the product alkanes may undergo reversion wherever the zone contains predominantly catalyst. Such reversion is undesirable and is to be avoided.

The feed to the process must contain at least one normal or mono-methyl-branched alkane containing from about 6 to about 8 carbon atoms. The feed may be predominately a single alkane or may be mixture of $C_6$ to $C_8$ alkanes. The feed may be largely normal alkanes, mono-methyl-branched alkanes, or a mixture thereof. Lighter hydrocarbons may be present, but will not produce the desired multi-methyl-branched alkanes. Examples of suitable alkanes include normal hexane, 2-methylpentane, 3-methylpentane, normal heptane, 2-methylhexane, 3-methylhexane, normal octane, 2-methylheptane, 3-methylheptane, and 4-methylheptane. Preferably the feed contains normal hexane, 2-methylpentane, 3-methylpentane, n-heptane, 2-methylheptane, 3-methylheptane, and 4-methylheptane. The feed is usually derived from other refinery processes and may contain some cyclic alkanes, olefinic hydrocarbons, aromatic hydrocarbons, and other hydrocarbons. The feed should not contain components that would significantly after the capacities or selectivities of the desorbent or that would deactivate the catalyst. The feed may also be the effluent of a fixed bed isomerization unit where alkane reactants and the corresponding isomerized products are present in amounts determined by the conversion in the fixed bed which is limited by thermodynamic equilibrium.

For catalyst stability, hydrogen must be introduced into the reaction and adsorption zone. The hydrogen may be introduced in a variety of ways, any of which would be appropriate so long as sufficient hydrogen is present where needed to provide the catalyst stabilizing function. The hydrogen to hydrocarbon mole ratio in the reaction and adsorption zone should be within a range from about 0.1 to about 2. The hydrogen may be introduced with or independently of the feed or the desorbent, and it may be introduced continuously or in a pulsed manner. For convenience, it is preferred that the hydrogen be introduced with and in the same manner as the desorbent. Note that high quantities of hydrogen alone would provide a desorption function, but the desorption would be weak and inefficient. Incomplete desorption of normal alkanes would require that the adsorbent be periodically regenerated. Therefore, in the present invention, the quantity of hydrogen is limited only to that which is needed for catalyst stability.

The desorbent must contain at least one normal or mono-methyl-branched alkane containing from about 4 to about 8 carbon atoms which is capable of desorbing the feed alkanes. Examples of acceptable alkanes for use in the desorbent include normal butane, 2-methylpropane, normal pentane, 2-methylbutane, normal hexane, 2-methylpentane, 3-methylpentane, normal heptane, 2-methylhexane, 3-methylhexane, normal octane, 2-methylheptane, 3-methylheptane, and 4-methylheptane. It is preferred that the desorbent alkane be capable of being isomerized since the branched alkanes which result from isomerization of the desorbent alkane are themselves octane boosters which may be blended into gasoline, thereby achieving an incremental octane number increase beyond that achieved through only isomerization of the alkanes present in the feed. For example, should normal pentane be used as a desorbent, 2-methylbutane would result as an incidental product. 2-Methylbutane is a valuable product in itself and may be blended with the gasoline pool to increase the octane number rating. Also the mono-methyl-branched $C_5$ alkanes may be used as intermediates after dehydrogenation for such oxygenate products as methyl tertiary butyl ether, ethyl tertiarybutyl ether, and tertiary amyl methyl ether. Therefore, the preferred desorbent alkane is a normal alkane and the most preferred is normal pentane.

The product stream withdrawn from the reaction and adsorption zone will contain the isomerized products of the feed, namely the multi-methyl-branched alkanes containing from about 6 to about 8 carbon atoms and desorbent. If the desorbent is isomerized, the product stream will contain a mixture of desorbent and isomerized products of the desorbent alkane.

The invention encompasses two different operational embodiments. In a first embodiment both the desorbent and the feed are introduced to the reaction and adsorption zone at a first end of the zone in a cocurrent flow mode. The feed is introduced as a pulse and the desorbent may be introduced continuously or the desorbent may be stopped momentarily while the pulse of feed is introduced. The reactants in the feed contact the catalyst and undergo isomerization to form mono-methyl-branched and multi-methyl-branched alkanes. Any normal or mono-methyl-branched alkanes are adsorbed by the adsorbent and the multi-methyl-branched alkanes are relatively unadsorbed and so are carried unhindered with the desorbent flow. At a second end of the reaction and adsorption zone, the product multi-methyl-branched alkanes are removed in a product stream as a mixture with desorbent. The normal or mono-methyl-branched alkanes are continuously being adsorbed and desorbed and therefore gradually move through the zone with the desorbent flow. As the normal or mono-methyl-branched alkanes are desorbed, they will contact the catalyst and continue to be isomerized. Eventually the front of normal or mono-methyl-branched alkanes will approach the second end of the zone where the product stream is being removed. At this time, the flow in the zone is reversed with the feed now being pulsed in at the second end, the desorbent also being introduced at the second end, and the product stream being removed from the first end. The concentration of normal and mono-methyl-branched alkanes are now in the region of the zone adjacent to the feed input and will not contaminate the product stream. Furthermore, the normal and mono-methyl-branched alkanes continue to remain in the zone and are able to contact the catalyst and be isomerized to form additional multi-methyl-branched products eliminating the need for recycle and reducing reactant waste. The process continues with the periodic reversal of fluid flow by alternating the input location of the desorbent and feed from one end of the zone to another and back.

The pulses of feed and the reversal of fluid flow in the zone are timed and the flowrates of the feed and desorbent controlled so that the normal and mono-methyl-branched alkanes do not contaminate the product stream and remain within the zone until they are isomerized to multi-methyl-branched alkanes. The alkane present in the desorbent may also undergo isomerization in the zone, but due to the volume of desorbent alkane present, it is expected that normal and mono-methyl-branched desorbent alkanes will be present in the product stream.

In the preferred operational embodiment of the invention, both the feed and desorbent are continuously introduced to the reaction and adsorption zone. Like the embodiment above, the desorbent is introduced to a first end of the reaction and adsorption zone. However, in this embodiment, the feed is introduced at about the center of the reaction and adsorption zone. It is important that the reaction and adsorption zone be symmetrically disposed about the point of feed introduction with respect to the size of the zone, the flow capacity of the zone, and especially the catalyst and adsorbent distribution within the zone. For example, if the zone were a series of six equally sized sequentially connected sub-beds each containing a homogeneous mixture of catalyst and adsorbent, the feed introduction point should be between the third and fourth sub-bed. The location of the feed remains constant during the process and can be described as dividing the zone into two equivalent portions.

Both the feed and the desorbent are continuously introduced to the reaction and adsorption zone. The reactants in the feed contact the catalyst and undergo isomerization to form mono-methyl-branched and multi-methyl-branched alkanes. Normal or mono-methyl-branched alkanes are adsorbed by the adsorbent and the multi-methyl-branched alkanes are relatively unadsorbed and so are carried unhindered with the desorbent flow. At a second end of the reaction and adsorption zone, the product multi-methyl-branched alkanes are removed in a product stream as a mixture with desorbent and perhaps isomerized desorbent alkane. As in the above embodiment, the normal or mono-methyl-branched alkanes are continuously being adsorbed and desorbed and therefore gradually move through the zone with the desorbent flow. As the normal or mono-methyl-branched alkanes are desorbed, they will contact the catalyst and continue to be isomerized. Eventually the front of normal or mono-methyl-branched alkanes will approach the second end of the zone where the product stream is being removed. At this time, the flow in the zone is reversed by introducing the desorbent at the second end of the zone instead of at the first end and removing the product stream from the first end of the zone. The location of the feed input remains constant. The concentration of normal and mono-methyl-branched alkanes is now in the region of the zone adjacent to the desorbent input and will not contaminate the product stream, and the normal and mono-methyl-branched alkanes remain in the zone and are able to contact the catalyst and be isomerized to form additional multi-methyl-branched products. In this embodiment the location of the feed input remains constant. The process continues with the periodic reversal of desorbent flow to keep the normal and mono-methyl-branched alkanes within the zone until they are isomerized to form multi-methyl-branched alkanes.

EXAMPLE 1

A single vessel was packed with 62.2 grams of a physical mixture of platinum on tungstated zirconia catalyst (25 mass %) and silicalite adsorbent (75 mass %) and held at 225° C. and 100 psig. Normal pentane at 0.33 cc/min and hydrogen at 55 cc/min were introduced at one end of the vessel and passed through the vessel as desorbent. The normal pentane flow was interrupted to introduce a 1 cc normal hexane as a pulse, after which the normal pentane flow was resumed. As the normal hexane passed though the vessel, it was reacted to form isomerized products which were then separated from normal and mono-methyl-branched alkanes. The effluent from the vessel was analyzed over time by gas chromatography and the results plotted. FIG. 1 shows that a high multi-methyl-branched fraction has been formed and separated, and eluted first. The high multi-methyl-branched fraction contained 69.6 mass % 2,2-dimethylbutane, 12.6 mass % 2,3-dimethylbutane, 10.2 mass % 2-methylpentane, 6.5 mass % 3-methylpentane, and 1.1 mass % normal hexane. In comparison, the content of the above components over the entire pulse experiment was 15.4 mass % 2,2-dimethylbutane, 9.0 mass % 2,3-dimethyl butane, 35.8 mass % 2-methylpentane, 21.8 mass % 3-methyl pentane, and 18.1 mass % normal hexane.

This experiment demonstrated that a high octane portion could be separated from a low octane portion, and that the high octane portion could be removed prior to the elution of the low octane portion

EXAMPLE 2

Figure 2:
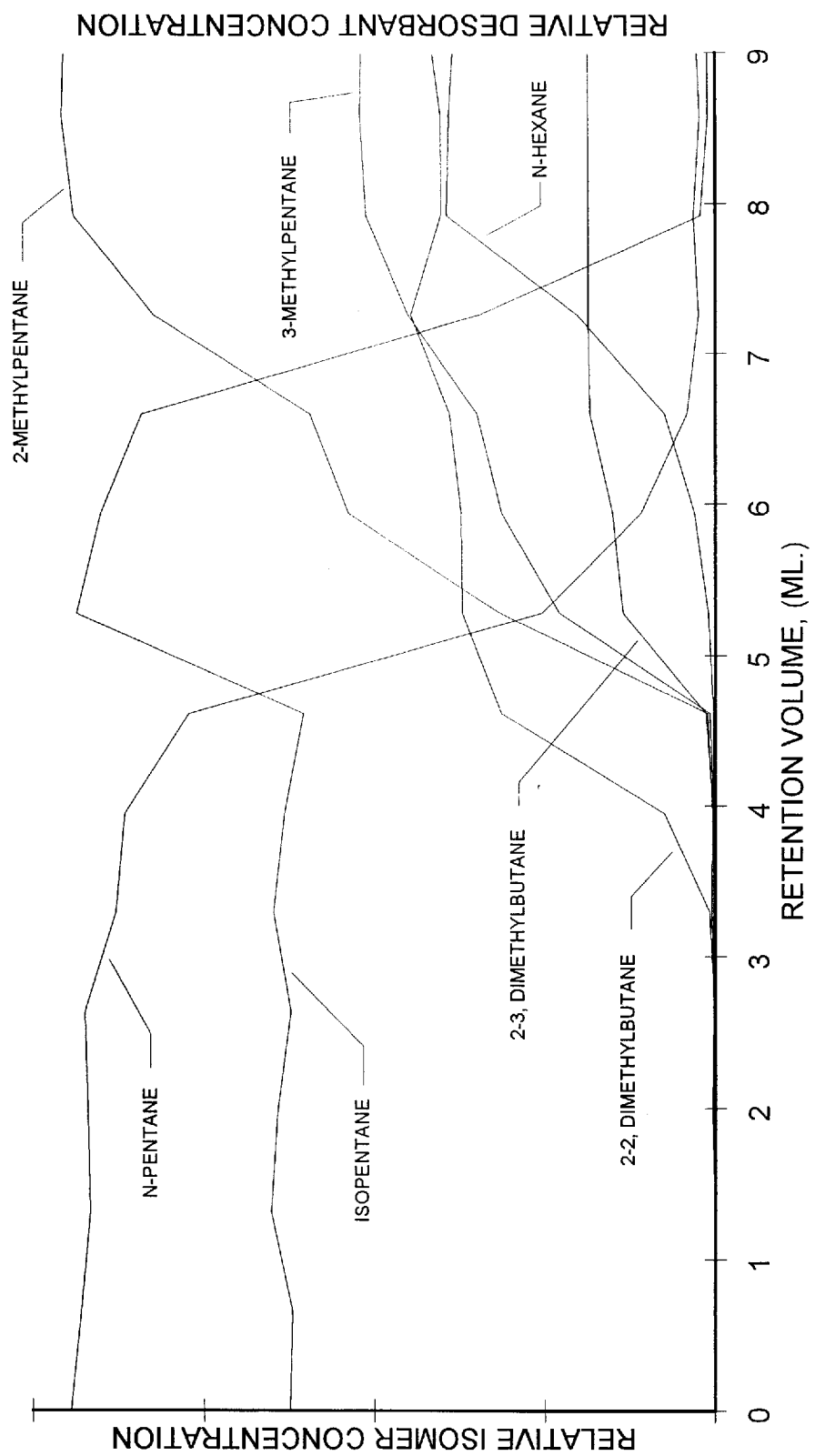
FIG. 2 is a chromatogram showing the results of the isomerization of a continuous normal hexane feed and the separation of a high multi-methyl-branched fraction from a mixture of normal, mono-methyl-branched and multi-methyl-branched alkanes using a mixture of platinum on sulfated zirconia and silicalite as conducted in Example 2.

A single vessel was packed with 64 grams of a physical mixture of platinum on sulfated zirconia catalyst (20 mass %) and silicalite adsorbent (80 mass %) and held at 175° C. and 100 psig. Normal pentane at 0.33 cc/min and hydrogen at 60 cc/min were continuously introduced at one end of the vessel and passed through the vessel as desorbent. A volume of normal hexane was introduced at the same end of the vessel as feed alkane by displacement with the normal pentane desorbent. As the normal hexane passed though the vessel, it was reacted to form isomerized products which were then separated from normal and mono-methyl-branched alkanes. The effluent from the vessel was analyzed over time by gas chromatography and the results plotted. FIG. 2 shows that dimethyl branched butanes are formed and separated from lower octane number normal and mono-methyl-branched compounds allowing for the isolation of high octane material.

EXAMPLE 3

Two sub-beds were each loaded with a homogeneous mixture containing a specified ratio of 20–40 mesh platinum on sulfated zirconia catalyst and 20–40 mesh adsorbent particles. The sub-beds were operated as a traditional unidirectional fixed bed at varying conditions; the sub-beds were not operated as reactive chromatography units. Normal pentane as desorbent and hydrogen were continuously introduced at a first end of the first sub-bed and passed through the sub-beds. Normal hexane feed was continuously introduced at a point between the two sub-beds. Product was withdrawn from the second end of the second sub-bed. As the normal hexane passed though the sub-beds, it was reacted to form isomerized products. The effluent from the vessels were condensed at −78° C. and analyzed by gas chromatography. Octane number was calculated from the resulting composition. Results are shown in Table 1 below.

The experiment was repeated, this time using reactive chromatography with periodic reversal of desorbent flow by discontinuing the introduction of the desorbent to the first end of the first sub-bed and instead, introducing the desorbent to the second end of the second sub-bed. Concurrently, the withdrawal of the product was also changed so that the product was now withdrawn from the first end of the first sub-bed instead of the second end of the second sub-bed. The effluent from the vessels was condensed and analyzed gas chromatography. The octane number was calculated from the resulting composition. Recovery was calculated by subtracting the amount of normal pentane and cracked products. The results are shown in Table 2 below.

In both Tables 1 and 2, "A" is the adsorbent selective pore volume, "AV" is the adsorbent volume, "CV" is the catalyst volume, "F" is the feed rate, "D" is the desorbent rate, "CT" is the cycle time in minutes, "LHSV" is the feed liquid hourly space velocity with regard to catalyst, "H2/HC" is the mole ratio of hydrogen to normal pentane, and "T" is temperature in degrees Celsius.

In comparing Tables 1 and 2, it is clear that in each case a higher product octane is obtained from the simultaneous reaction and separation than with fixed bed conversion. In particular, the effluent of 2,2-dimethyl butane is dramatically higher with reactive chromatography than for the fixed bed, thus showing attainment of supra-equilibrium effluent.

TABLE 1

| ADSORBENT | T | PSIG | CV/AV | LHSV | D/F | H2/HC | IC5/ TOTAL C5 | 2,2-DIMETHYL BUTANE/ TOTAL C6 | N-C6/ TOTAL C6 | PRODUCT OCTANE |
|---|---|---|---|---|---|---|---|---|---|---|
| Silicalite | 200 | 100 | 0.24 | 1.3 | 1.5 | 0.49 | 71.3 | 9.8 | 20.7 | 77.5 |
| NaX | 175 | 50 | 0.15 | 1.2 | 2.0 | 0.47 | 73.6 | 21.7 | 14.2 | 84.4 |
| Silicalite | 175 | 50 | 0.15 | 0.8 | 3.2 | 0.50 | 69.2 | 16.0 | 15.9 | 82.9 |

TABLE 2

| ADSORBENT | T | PSIG | CV/AV | CT | A/F | D/F | H2/HC | I-C5/ TOTAL C5 | 2,2-DIMETHYL BUTANE/ TOTAL C6 | N-C6/ TOTAL C6 | PRODUCT OCTANE |
|---|---|---|---|---|---|---|---|---|---|---|---|
| Silicalite | 200 | 100 | 0.24 | 30 | 1.04 | 1.55 | 0.63 | 45.1 | 20.0 | 13.4 | 85.2 |
| Silicalite | 200 | 100 | 0.24 | 30 | 2.08 | 3.10 | 0.75 | 35.3 | 36.4 | 5.8 | 89.7 |
| Silicalite | 200 | 100 | 0.24 | 30 | 2.08 | 4.10 | 0.60 | 37.1 | 33.9 | 4.8 | 90.0 |
| NaX | 175 | 50 | 0.15 | 32.7 | 2.87 | 2.00 | 0.51 | 41.0 | 37.6 | 9.7 | 86.7 |
| NaX | 175 | 50 | 0.15 | 36 | 2.60 | 2.00 | 0.47 | 44.9 | 37.2 | 9.5 | 87.7 |
| NaX | 175 | 50 | 0.15 | 36 | 3.91 | 3.35 | 0.53 | 46.8 | 43.6 | 7.7 | 89.9 |
| NaX | 175 | 50 | 0.15 | 38 | 2.47 | 2.00 | 0.47 | 42.1 | 31.6 | 10.8 | 86.1 |
| Silicalite | 175 | 50 | 0.15 | 36 | 1.79 | 3.09 | 0.54 | 44.2 | 30.3 | 7.2 | 89.0 |
| Silicalite | 175 | 50 | 0.15 | 36 | 1.79 | 5.64 | 0.32 | 49.8 | 14.3 | 11.3 | 88.2 |

What is claimed is:

1. A process for isomerizing at least one normal or mono-methyl-branched alkane containing from about 6 to about 8 carbon atoms to form at least one multi-methyl-branched alkane comprising:

a) introducing a pulse of feed containing said normal or mono-methyl-branched alkane to a first end of a reactive chromatography fixed bed reaction and adsorption zone containing a hydrogen atmosphere at a mole ratio of hydrogen to hydrocarbon in the range of about 0.1 to about 2, a catalyst effective to isomerize the normal or mono-methyl-branched alkane, and an adsorbent effective to selectively adsorb normal and mono-methyl-branched alkanes relative to multi-methyl-branched alkanes, and operating under conditions effective to isomerize the normal or mono-methyl-branched alkane;

b) introducing a desorbent comprising at least one alkane having from about 4 to about 8 carbon atoms to the first end of said zone and withdrawing an effluent containing at least one multi-methyl-branched alkane from a second end of said zone;

c) reversing, after a period of time, fluid flow in the zone by redirecting the introduction of the desorbent and a second pulse of feed to the second end of said zone and concurrently moving the location of the withdrawal of the effluent to the first end of said zone to retain said normal and mono-methyl-branched alkanes within the zone for isomerization; and d) continuing to periodically reverse fluid flow in the zone by alternating introducing the desorbent and additional pulses of feed to the first end and then the second end of said zone while concurrently withdrawing the effluent from the second end and then the first end of said zone to retain said normal and mono-methyl-branched alkanes within the zone for isomerization.

2. The process of claim 1 wherein the catalyst and adsorbent are present in the zone as a homogeneous mixture.

3. The process of claim 1 wherein the desorbent is normal pentane.

4. The process of claim 1 wherein the catalyst is selected from the group consisting of platinum on mordenite, aluminum chloride on alumina, platinum on sulfated zirconia, and platinum on tungstated zirconia.

5. The process of claim 1 wherein the catalyst is platinum on tungstated zirconia.

6. The process of claim 1 wherein the catalyst is platinum on sulfated zirconia.

7. The process of claim 1 wherein the adsorbent is selected from the group consisting of zeolites having the structural framework of X, Y, or beta, and ion exchanged with sodium, potassium, calcium, strontium barium, and mixtures thereof, and silicalite, ferrierite and mixtures thereof.

8. The process of claim 1 wherein the normal or mono-methyl-branched alkane is a mixture of alkanes containing 6 or 7 carbon atoms and the adsorbent is silicalite.

9. The process of claim 1 wherein the normal or mono-methyl-branched alkane is an alkane or mixture of alkanes containing 6 carbon atoms and the adsorbent is X-zeolite exchanged with sodium.

10. The process of claim 1 wherein the normal or mono-methyl-branched alkane is an alkane or mixture of alkanes containing 7 carbon atoms and the adsorbent is X-zeolite exchanged with sodium.

11. A process for isomerizing at least one normal or mono-methyl-branched alkane containing from about 6 to about 8 carbon atoms to form at least one multi-methyl-branched alkane comprising:

a) introducing a feed containing said normal or mono-methyl-branched alkane to a reactive chromatography fixed bed reaction and adsorption zone containing a hydrogen atmosphere at a mole ratio of hydrogen to hydrocarbon in the range of about 0.1 to about 2, a catalyst effective to isomerize the normal or mono-methyl-branched alkane, and an adsorbent effective to selectively adsorb normal and mono-methyl-branched alkanes relative to multi-methyl-branched alkanes, and operating under conditions effective to isomerize the normal or mono-methyl-branched alkane, said feed being continually introduced to the reaction and adsorption zone at a location where the reaction and adsorption zone is symmetrically disposed about said feed introduction point with respect to the size of the zone, the flow capacity of the zone, and the catalyst and adsorbent distribution;

b) introducing a desorbent comprising at least-one alkane having from about 4 to about 8 carbon atoms to a first end of said zone and withdrawing an effluent containing at least one multi-methyl-branched alkane from a second end of said zone;

c) reversing, after a period of time, fluid flow in the zone by redirecting the introduction of the desorbent to the second end of said zone and concurrently moving the location of the withdrawal of the effluent to the first end of said zone to retain said normal and mono-methyl-branched alkanes within the zone for isomerization; and d) continuing to periodically reverse fluid flow in the zone by alternating introducing the desorbent to the first end and then the second end of said zone while concurrently withdrawing the effluent from the second end and then the first end of said zone to retain said normal and mono-methyl-branched alkanes within the zone for isomerization.

12. The process of claim 11 wherein catalyst and adsorbent are present in the zone as a homogeneous mixture.

13. The process of claim 11 wherein the desorbent is normal pentane.

14. The process of claim 11 wherein the catalyst is selected from the group consisting of platinum on mordenite, aluminum chloride on alumina, platinum on sulfated zirconia, and platinum on tungstated zirconia.

15. The process of claim 11 wherein the catalyst is platinum on tungstated zirconia.

16. The process of claim 11 wherein the catalyst is platinum on sulfated zirconia.

17. The process of claim 11 wherein the adsorbent is selected from the group consisting of zeolites having the structural framework of X, Y, or beta, and ion exchanged with sodium, potassium, calcium, strontium, barium, and mixtures thereof, and silicalite, ferrierite and mixtures thereof.

18. The process of claim 11 wherein the normal or mono-methyl-branched alkane is a mixture of alkanes containing 6 or 7 carbon atoms and the adsorbent is silicalite.

19. The process of claim 11 wherein the normal or mono-methyl-branched alkane is an alkane or mixture of alkanes containing 6 carbon atoms and the adsorbent is X-zeolite exchanged with sodium.

20. The process of claim 11 wherein the normal or mono-methyl-branched alkane is an alkane or mixture of alkanes containing 7 carbon atoms and the adsorbent is X-zeolite exchanged with sodium.

* * * * *